(12) United States Patent
Teber et al.

(10) Patent No.: US 10,799,709 B2
(45) Date of Patent: Oct. 13, 2020

(54) PORTABLE SINGLE USE AUTOMATED EXTERNAL DEFIBRILLATOR DEVICE

(71) Applicant: CellAED Life Saver Pty Ltd, Elanora Heights, NSW (AU)

(72) Inventors: Erol Teber, Ryde (AU); Donovan Casey, Elanora Heights (AU)

(73) Assignee: CellAED Life Saver Pty Ltd, Elanora Heights (AU)

( * ) Notice: Subject to any disclaimer, the term of this patent is extended or adjusted under 35 U.S.C. 154(b) by 60 days.

(21) Appl. No.: 16/077,256

(22) PCT Filed: Jun. 20, 2018

(86) PCT No.: PCT/AU2018/050607
§ 371 (c)(1),
(2) Date: Aug. 10, 2018

(87) PCT Pub. No.: WO2018/232450
PCT Pub. Date: Dec. 27, 2018

(65) Prior Publication Data
US 2019/0329057 A1    Oct. 31, 2019

(30) Foreign Application Priority Data
Jun. 20, 2017 (AU) .................................. 2017902350

(51) Int. Cl.
*A61N 1/39* (2006.01)
*A61N 1/04* (2006.01)

(52) U.S. Cl.
CPC ........... *A61N 1/3925* (2013.01); *A61N 1/046* (2013.01); *A61N 1/3975* (2013.01); *A61N 1/3904* (2017.08)

(58) Field of Classification Search
CPC .... A61N 1/3925; A61N 1/3975; A61N 1/046; A61N 1/3904; A61N 1/3968
See application file for complete search history.

(56) References Cited

U.S. PATENT DOCUMENTS 5,817,151 A * 10/1998 Olson .................. A61N 1/3931
607/142
5,871,505 A    2/1999 Adams et al.
(Continued)

FOREIGN PATENT DOCUMENTS

CN           101745180         6/2010
EP         2450082 A1         5/2012
(Continued)

OTHER PUBLICATIONS

International Search Report & Written Opinion dated Jul. 27, 2018 from PCT Application No. PCT/AU2018/050607.
(Continued)

*Primary Examiner* — Rex R Holmes
(74) *Attorney, Agent, or Firm* — Dentons US LLP

(57) ABSTRACT

There is provided herein a small form factor portable automatic external defibrillator (AED) having a controller, a charging circuit and a discharge circuit to discharge capacitors using a respective pair of electrode pads. The defibrillator may be separable into two portions at a bisection. Each portion may have a respective electrode pad on corresponding upper surfaces thereof for electrical contact with the chest. A circuit completion wire may complete the electric circuit between the two portions. The defibrillator may comprise a peel-off layer covering both adjacent electrodes. The peel-off layer is adhered to the board at peripheral edges thereof. As such, when pressure is applied to the bisection, the board snaps into the two portions and the peel-off layer simultaneously peels from the portions. In this way, the defibrillator may be deployed quickly with a single break apart manoeuver.

17 Claims, 8 Drawing Sheets

(56) References Cited

U.S. PATENT DOCUMENTS

| | | | |
|---|---|---|---|
| 5,908,443 | A | 6/1999 | Brewer et al. |
| 6,353,758 | B1 * | 3/2002 | Gliner .................. A61N 1/39 607/5 |
| 6,456,877 | B1 | 9/2002 | Fishler |
| 6,539,255 | B1 | 3/2003 | Brewer et al. |
| 8,615,295 | B2 * | 12/2013 | Savage ................ A61N 1/046 607/5 |
| 10,226,615 | B2 | 3/2019 | Lang et al. |
| 2004/0260376 | A1 | 12/2004 | Craige et al. |
| 2005/0244709 | A1 | 11/2005 | Bucher |
| 2009/0240297 | A1 | 9/2009 | Shavit et al. |
| 2010/0241181 | A1 | 9/2010 | Savage et al. |
| 2012/0310315 | A1 | 12/2012 | Savage et al. |
| 2014/0039593 | A1 | 2/2014 | Savage et al. |
| 2014/0107718 | A1 | 4/2014 | Foote et al. |
| 2014/0317914 | A1 | 10/2014 | Shaker |
| 2016/0271408 | A1 | 9/2016 | Newton et al. |
| 2017/0157415 | A1 | 6/2017 | Horseman et al. |

FOREIGN PATENT DOCUMENTS

| | | |
|---|---|---|
| WO | 2001010496 | 2/2001 |
| WO | 2007069162 | 6/2007 |
| WO | 2007135599 | 11/2007 |
| WO | 2008057302 | 5/2008 |
| WO | 2010146492 | 12/2010 |
| WO | 2015143460 | 10/2015 |
| WO | 2016092800 A1 | 6/2016 |
| WO | 2016149680 | 9/2016 |

OTHER PUBLICATIONS

Okamura et al., "Evaluation of a Unique Defibrillation Unit with Dual-Vector Biphasic Waveform Capabilities: Towards a Miniaturized Defibrillator," Pace, Published Feb. 2017, pp. 108-114, vol. 40.

Dames, J.S., "Monophasic vs Biphasic Waveform Defibrillation," AED Superstore Website, published on Mar. 3, 2016 [online], retrieved from <URL:https://www.aedsuperstore.com/resources/monophasic-vs-biphasic/ [retrieved on Aug. 14, 2019], 9 pages.

* cited by examiner

PORTABLE SINGLE USE AUTOMATED EXTERNAL DEFIBRILLATOR DEVICE

FIELD OF THE INVENTION

The present invention relates to portable automated external defibrillators (AEDs).

BACKGROUND OF THE INVENTION

Defibrillation is treatment for life-threatening cardiac dysrhythmias such as ventricular fibrillation (VF) and non-perfusion ventricular tachycardia (VT).

An automated external defibrillator (AED) delivers electric current (referred to as countershock) to the heart which polarises the heart muscle, and in the dysrhythmia allowing the sinoatrial node to re-establish the normal sinus rhythm.

It is estimated that in OECD countries, approximately only one AED device is available per square kilometre. Furthermore, such AED devices are large, costly and sometimes in excess of $2000 each and furthermore require regular maintenance, testing and calibration.

As such, a need therefore exists for portable AED devices which are more readily accessible for improving survival rates.

The present invention seeks to provide a portable, lightweight, small, single use, relatively inexpensive AED device, which will overcome or substantially ameliorate at least some of the deficiencies of the prior art, or to at least provide an alternative.

US 2014/0107718 A1 (HEARTLIFE TECHNOLOGY, LLC) 17 Apr. 2014 [hereinafter referred to as D1] discloses an automated defibrillator module attachment for a smart phone which may interface with the headphone jack thereof. In embodiments, the module takes the form of a phone case which may be split into two coupling members each having a defibrillator pad.

US 2009/0240297 A1 (SHAVIT et al.) 24 Sep. 2009 [hereinafter referred to as D2] similarly discloses a defibrillator unit and second electronic pad which is disassembled from a handheld phone device for application.

US 2016/0271408 A1 (CARDIOSPARK LLC) 22 Sep. 2016 [hereinafter referred to as D3] similarly discloses a portable automated defibrillator unit have any housing separable into two pieces for delivering countershock.

It is to be understood that, if any prior art information is referred to herein, such reference does not constitute an admission that the information forms part of the common general knowledge in the art, in Australia or any other country.

SUMMARY

There is provided herein a small form factor portable automatic external defibrillator (AED) being configured for ready access and quick deployment.

The defibrillator comprises a controller and a charging circuit controlled by the controller to charge at least one capacitor using a battery. The defibrillator further comprises a discharge circuit controlled by the controller to discharge the capacitors using a pair of electrode pads.

In one embodiment, the defibrillator is especially suited for rapid deployment wherein the defibrillator comprises a board separable into two portions at a bisection. Each portion has a respective electrode pad on corresponding upper surfaces thereof for electrical contact with the chest. A circuit completion wire may complete the electric circuit between the two portions.

The defibrillator may comprise a peel-off layer covering both adjacent electrodes. The peel off layer is adhered to the board at peripheral edges thereof. As such, when pressure is applied to the bisection, the board snaps into the two portions and the peel-off layer simultaneously peels from the portions. In this way, the defibrillator may be deployed quickly with a single break apart manoeuvre.

Proximal edges of the electrodes adjacent the bisection may be electrically connected via electrical connections stubs to respective portions of the board such that the opposite respective distal edges thereof are free to move away from the distal ends of the respective portions so as to more closely follow the contours of the chest to enhance the electrical connection of the pads. Lateral flexible retainers may retain the edges of the electrode pads the respective edges of the portions. In embodiments the peel-off layer is electrically conductive and remains connected to the lateral edges of the board, negating the need for a separate ground wire.

In embodiments, the charging circuit is configured for delivering a biphasic waveform comprising a positive step change exponential decay phase followed by a negative step change exponential decay phase. In accordance with this embodiment, the charging/discharge circuit may comprise a pair of capacitors which simplifies the switching requirements of the charging circuit because the polarity of a capacitor does not need to be reversed, thereby avoiding high current switching typically requiring isolated-gate bipolar transistors (IGBTs) which are bulky and relatively expensive. As such, the present dual capacitor bank charge/discharge circuit allows for a smaller defibrillator device, especially suited for small form factor portable packaging requirements.

According to one aspect, there is provided a portable automatic external defibrillator comprising: a controller; a charging circuit controlled by the controller to charge at least one capacitor using a battery; a discharge circuit controlled by the controller to discharge the capacitors using a pair of electrode pads; a board separable into two portions at a bisection, each portion having a respective electrode pad on an upper surface thereof.

The defibrillator may further comprise a peel-off layer covering the electrodes adjacently and adhered to the board at peripheral edges thereof such that when pressure is applied at the bisection, the board separates into the two portions and the peel-off layer simultaneously peels from the two portions and wherein the controller is configured for detecting the board separated into the two portions and controlling the discharge circuit to deliver a countershock waveform via the electrode pads.

The electrode pads may be flexible and wherein the two portions may be substantially rigid and wherein the electrode pads may be electrically connected to respective portions at proximal edges thereof adjacent the bisection such that the respective opposite lateral edges thereof may be free to follow chest contours.

The defibrillator may further may comprise flexible retainers retaining the lateral edges to respective portions.

The peel-off layer may be electrically conductive or comprise integral circuit completion wiring, and wherein the peel-off layer remains connected to lateral edges of the portions such that when the portions may be broken apart and inverted to contact the chest, the peel-off layer electrically connects the portions.

The controller and charging and discharging circuits may be located between respective electrode pads and portions.

The electrodes may comprise electrically conductive gel layers.

The charging circuit comprises a first capacitor and a second capacitor and wherein the controller may be configured for controlling the discharge circuit to deliver a positive step change exponential decay current phase using the first capacitor and a subsequent negative step change exponential decay current phase using the second capacitor.

The discharge circuit comprises a first switch operably coupled to the first capacitor and a second switch operably coupled to the second capacitor and wherein the discharge circuit operates the switches in turn.

The phases each have a peak voltage amplitude of approximately 1 kV.

The first capacitor may have a greater capacitance than that of the second capacitor and wherein the positive step change exponential decay current phase may have a duration greater than that of the negative step change exponential decay phase.

The first capacitor may be approximately 60 µF and wherein the second capacitor may be between approximately 20-60 µF.

The positive exponential decay current waveform may have a duration of between approximately 6-9 ms.

According to another aspect, there is provided a method using a portable automatic external defibrillator comprising: a controller; a charging circuit controlled by the controller to charge at least one capacitor using a battery; a discharge circuit controlled by the controller to discharge the capacitors using a respective pair of electrode pads; bifurcated board having a bisection defining two portions, each portion having a respective electrode pad on an upper surface thereof; a peel-off layer covering the electrodes adjacently and adhered to the board at peripheral edges thereof, the method comprising separating the two portions of the board at the bisection and rotating each portion to peel the peel-off layer from the two portions and to expose the electrode pads to place the portable automatic external defibrillator in a condition ready for use.

The method may otherwise comprise moving the portions apart to detach the peel-off layer from both portions.

Alternatively, the peel-off layer may be electrically conductive and wherein the method may otherwise comprise leaving the peel-off layer electrically connected between edges of the portions.

In this regard, the charging circuit may comprise a pair of capacitors

BRIEF DESCRIPTION OF THE DRAWINGS

Notwithstanding any other forms which may fall within the scope of the present invention, preferred embodiments of the disclosure will now be described, by way of example only, with reference to the accompanying drawings in which.

DESCRIPTION OF EMBODIMENTS

Figure 1:
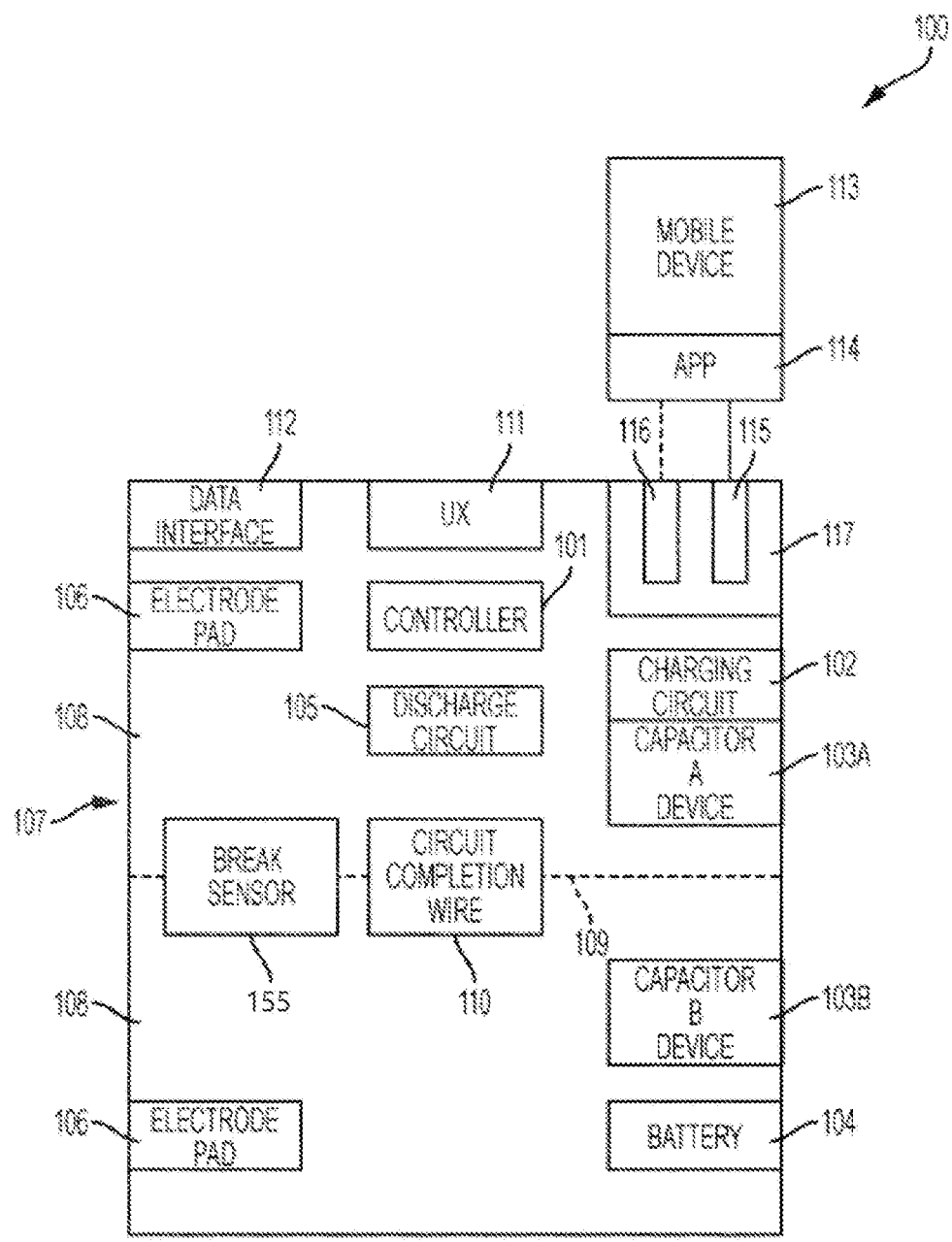
FIG. 1 shows a functional schematic of the componentry of a portable automated external defibrillator device in accordance with an embodiment.

FIG. 1 shows a functional schematic of an automated external defibrillator (AED) 100. The defibrillator 100 comprises a controller 101 for controlling the operation thereof. The controller 101 may control the charging circuit 102 which may charge a pair of capacitors 103 using a battery 104.

The controller 101 may further control the discharge circuit 105 which may discharge the charged capacitors 103 via a pair of electrode pads 106 to deliver countershock electric current.

In embodiments, the defibrillator 100 may comprise a board 107 separable into two portions 108 at a weakening bisection 109 therebetween. The controller 101 may detect the separation of the portions 108 using a break sensor 155 operative across the bisection 109. Each portion 108 comprises a separate electrode pad 106 which may be placed across the chest to deliver the countershock. A circuit completion wire 110 may electrically connect the portions 108.

In embodiments, the controller 101 comprises analogue circuitry. However, in another embodiment, the controller 101 has a low power microprocessor having memory having computer program code instructions therein for controlling the operation of the controller 101.

In embodiments, a user interface 111 may interface with the controller 101 for outputting information to the user and for receiving user interface input. In this way, the user interface 111 may instruct the user as to the proper application of defibrillation and receive user responses. In embodiments, the user interface 111 may comprise an audio output device for output of instructional audio. In embodiments, the user interface 111 may comprise a digital display, such as a small form factor LED digital display for the output of instructional information. User interface 111 may further comprise at least one of a plurality of control buttons and/or digital display haptic overlay for receiving user interface instructions.

In embodiments, the defibrillator 100 may comprise a data interface 112 for sending and receiving digital data across a computer data network, such as a short-range Bluetooth interface, longer range GSM data network or the like. The data interface 112 may be configured for transmitting data indicative of the operation of the defibrillator 100 and additional information such as electrocardiograph (ECG) statistics, waveforms, location information (such as which may be determined using a GPS receiver, not shown) and the like.

In embodiments, the defibrillator 100 may interface with a mobile phone device 113. The mobile phone device 113 may execute a software application 114 for implementing the functionality associated with the defibrillator 100. The mobile phone device 113 may interface with a wired interface 115 (such as USB) or a wireless interface 116 (such as a Bluetooth wireless interface) of an I/O interface 117 of the defibrillator 100.

Figure 2:
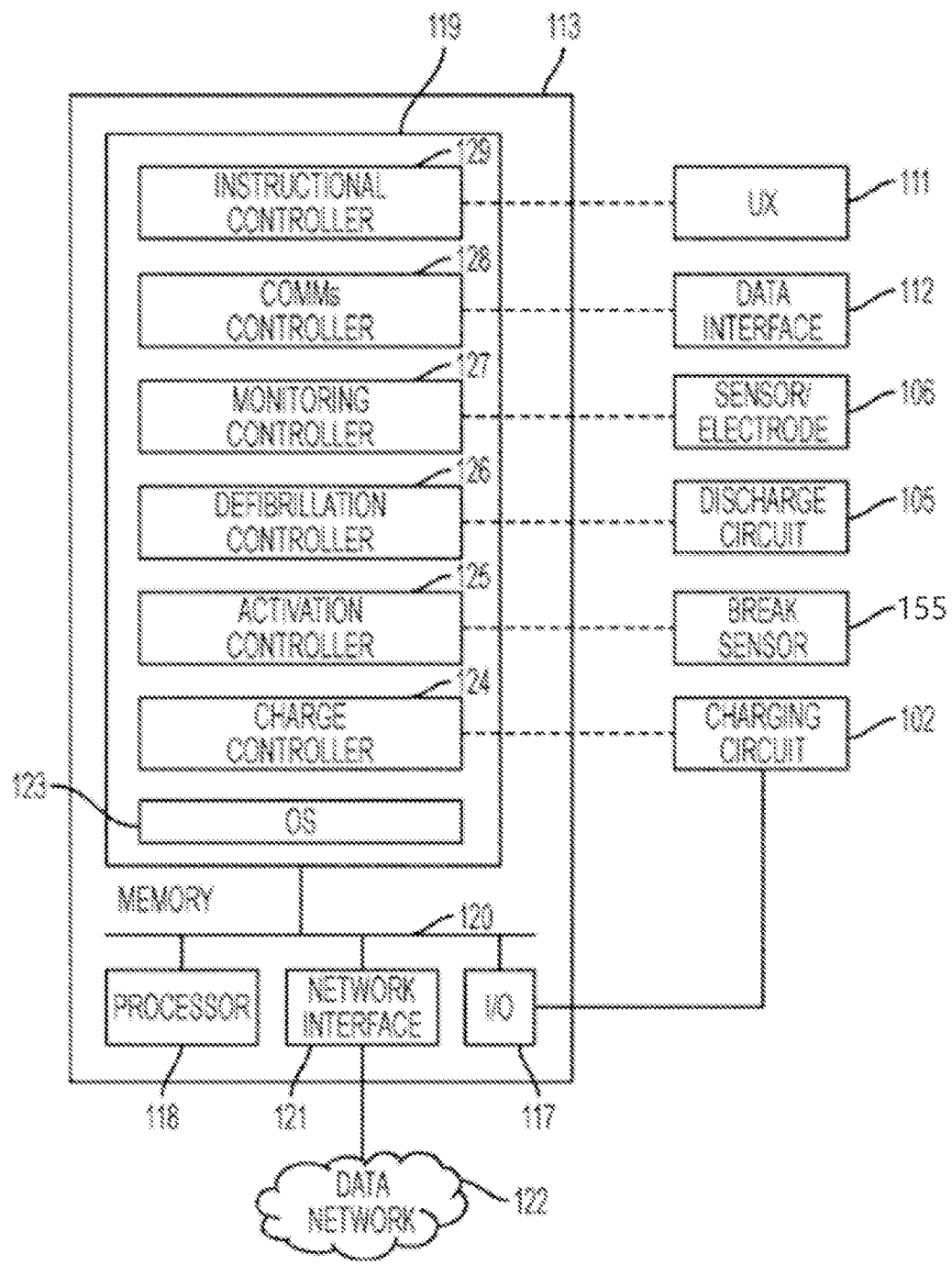
FIG. 2 shows a functional schematic of various operational controllers of the portable automated external defibrillator device in accordance with an embodiment.

FIG. 2 illustrates the interaction between the mobile phone device 113 and the various components of the defibrillator 100.

As can be seen, the mobile device 113 comprises a processor 118 for processing digital data and a memory device 119 operably coupled thereto across a system bus 120.

The memory device 119 comprises computer program code instructions which are fetched, decoded and executed by the processor 118 in use. The mobile device 113 may further comprise a network interface 121 for sending and receiving data across a GSM network 122. Furthermore, the mobile device 113 may comprise the I/O interface 117 for interfacing with the various components of the defibrillator 100.

The memory device may comprise an operating system 123 upon which the software application 114 executes. For illustrative convenience, the computer program code instructions of the software application 114 are shown as having been divided into various control modules. In this regard, the controllers may comprise a charge controller 124 for controlling the charging circuit 102 to charge the capacitors 103. The controllers may further comprise an activation controller 125 for controlling the activation of the defibrillator 100. In embodiments, the activation controller 125 may interface with the break sensor 155 so as to detect the separation of the portions 108. The activation controller 125 may then control the charge controller 124 to charge the capacitors 103 using the battery 104.

In embodiments, the activation controller 125 may monitor resistance between the electrode pads 106. For example, when the defibrillator is peeled or broken into two portions as is described hereunder, the activation controller 125 may detect the loss of conductivity between the electrode pads 106 and therefore control the charge controller 124 to begin charging the capacitors 103. Thereafter, when detecting conductivity between the electrode pads 106 within a resistance range, indicative of the electrode pads 106 having been placed on the chest, the activation controller may control a defibrillation controller 126 to control the discharge circuit 105 to discharge the capacitors 103 via the electrode pads 106.

The monitoring controller 127 may monitor ECG signals via the electrode pads 106 so as to be able to detect treatable rhythms and control the defibrillation controller 126 accordingly.

The communication controller 128 may further send and receive data across the network interface 121 or the data interface 112 of the defibrillator 100. In embodiments, the communication controller 128 may send data indicative of the defibrillator 100, including location information, patient identification information and the like relevant for first responders. Furthermore, the communication controller 128 may send ECG diagnostic information such as waveforms, statistics and the like for remote diagnostic assistance.

An instructional controller 129 may further interface with the user interface 111 or alternatively user interface of the mobile device 113 to output instructional information and receive user responses. For example, the instructional controller 129 may instruct the user as to the placement of the electrode pads 112, inform the user when the charging circuit 102 has charged the capacitors 103 and therefore to stand clear, when discharges are taking place, the status of defibrillation, the re-establishment of a normal sinus rhythm and the like.

At each stage, the user may input responses such as confirmation of having placed the electrodes correctly, confirmation of having stood clear and the like. Such user interface responses may be via haptic interaction with buttons or haptic overlay of the user interface 111 of the defibrillator 100 or the mobile device 113 itself. In embodiments, the instructional controller 129 may employ speech-to-text recognition so as to allow for verbal user interface feedback.

It should be noted that whereas the controllers are described in FIG. 2 as being implemented by the mobile device 113, in embodiments of the defibrillator 100 may be configured for stand-alone application without an attendant mobile device 113 and therefore the defibrillator 100 itself may comprise a memory device having the relevant controllers.

Figure 3:
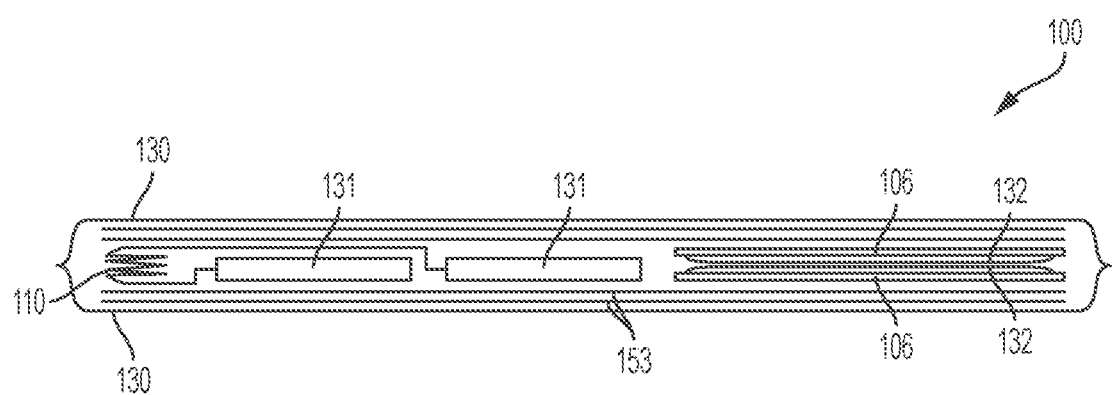
FIG. 3 illustrates a single use defibrillator packaging in accordance with an embodiment.
Figure 4:
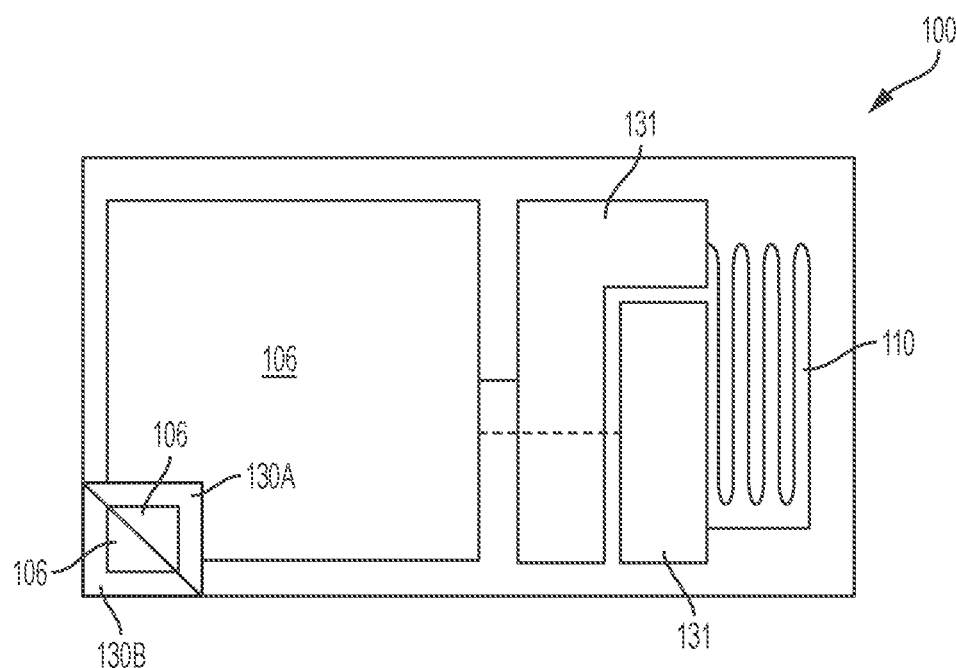
FIGS. 4 and 5 illustrate the deployment of the defibrillator of the embodiment of FIG. 3.

FIG. 3 illustrates a side elevation view of a single use defibrillator 100 in accordance with one embodiment. FIG. 4 illustrates a top plan view thereof.

In accordance with this embodiment, the defibrillator 100 comprises a peel off layer 130 and, specifically, a pair of peel off layer is 130 which may be peeled apart into two portions 108.

As is shown, the defibrillator 100 comprises various planar electrical componentry 131 which may comprise the controller 101, discharge circuit 105, charging circuit 102, batteries 104, capacitors 103 and the like. As is shown in FIG. 4, the componentry may fit together in a plane so as to minimise the thickness of the defibrillator 100. As is further shown, the defibrillator comprises the electrode pads 106. As can be seen, the electrode pads 106 occupy a significant surface area of the defibrillator 100 so as to enhance the electrical connection to the chest. Layers of electrically conductive gel 132 may cover each pad 106 to enhance the electrical connection.

The defibrillator 100 further comprises the circuit completion wire 110 electrically connecting the two portions 108.

In embodiments, inbuilt capacitive layers 153 (such as of metallic foil and suitable dielectric material therebetween) may locate atop, beneath or around the peel off layer 130 so as to store charge so as to take the form of the capacitors 103 or to enhance the capacitive capacity thereof. In this embodiment, the various componentry remains electrically connected to these inbuilt capacitive layers 153 for the discharge of energy therefrom.

FIG. 4 illustrates the peeing away of the upper peel off layer 130A from the lower peel off layer 130B so as to expose the electrode pads 106 therebetween.

Figure 5:
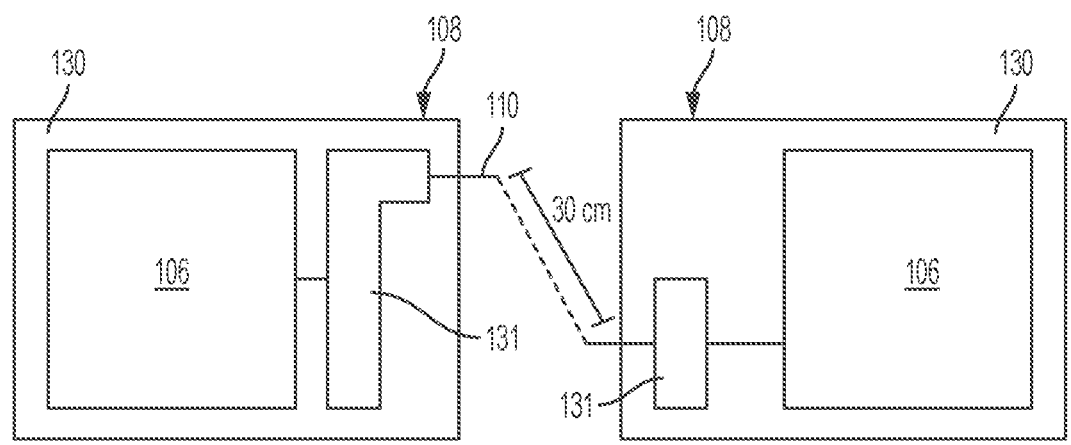

FIG. 5 illustrates the separation of the two portions 108 and the exposure of a respective electrode pad 106.

Figure 6:
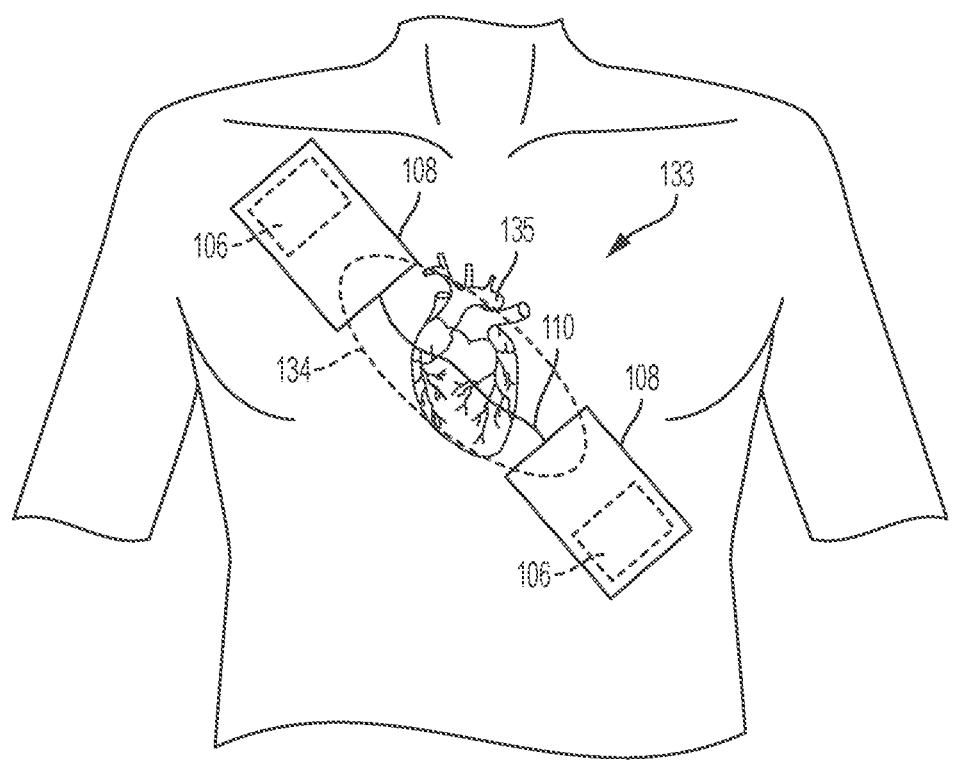
FIG. 6 illustrates the placement of the portions of the defibrillator across the chest.

FIG. 6 illustrates the placement of the portions 108 across the chest 133 to deliver countershock current 134 across the heart 135. Each portion 110 may be electrically connected by the circuit completion wire 110.

Figure 9:
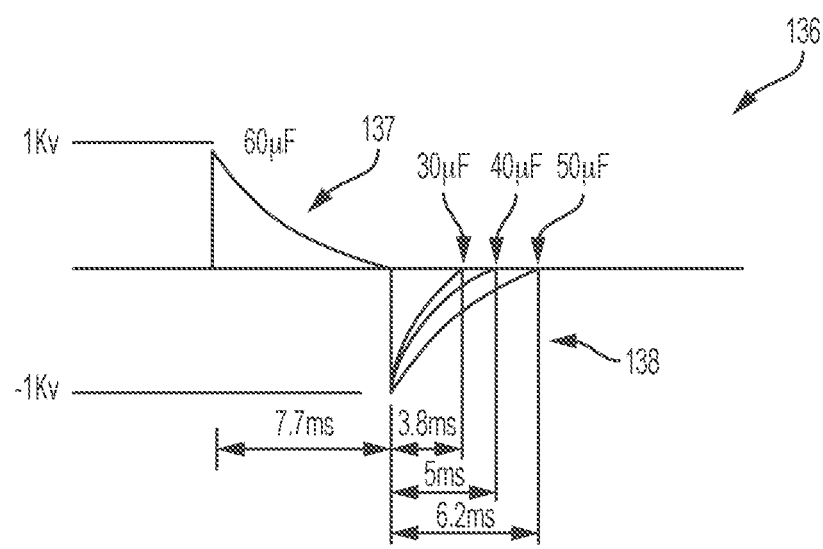
FIG. 9 illustrates a biphasic countershock current waveform in accordance with a preferred embodiment.

FIG. 9 illustrates a biphasic waveform countershock current 136 delivered by the defibrillator 100 in accordance with a preferred embodiment. The countershock current 136 comprises a positive step change exponential decay current phase 137 having an amplitude of approximately 1 kV. At approximately zero, the current 136 further comprises a step change negative exponential decay waveform phase 138 of approximately −1 kV.

Figure 7:
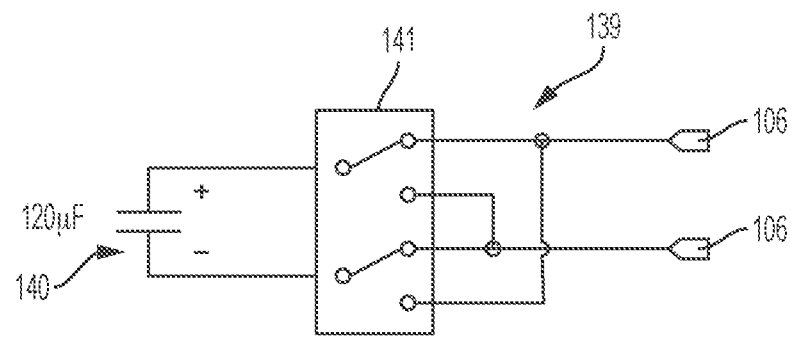
FIG. 7 illustrates a single capacitor charge/discharge circuit.
Figure 8:
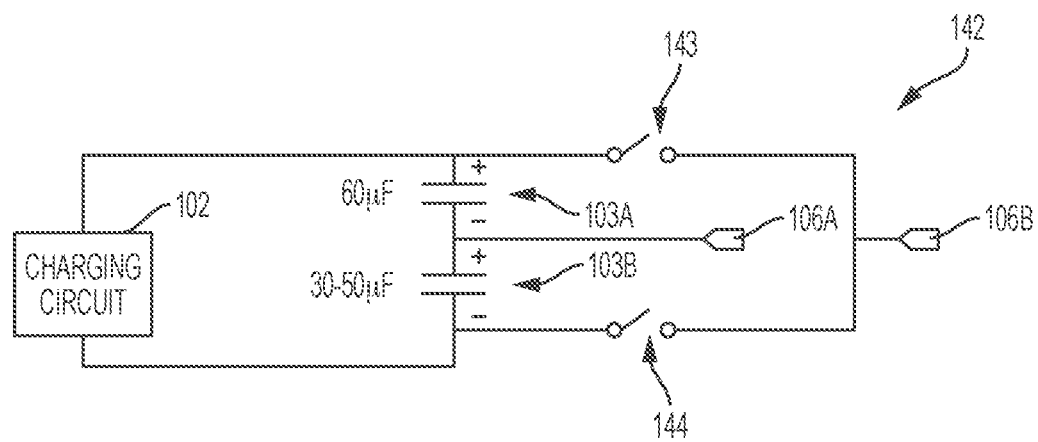
FIG. 8 illustrates a dual capacitor charge/discharge circuit in accordance with a preferred embodiment.

FIG. 7 illustrates a single capacitor circuit 139 comprising a single capacitor 140 and double throw insulated-gate bipolar transistor (IGBT) switching 141 interfacing the single capacitor 140 and the electrode pads 106. The switching 141 may be controlled to switch midway a discharge of the single capacitor 140 so as to reverse the polarity applied to the electrode pads 106 to achieve the biphasic waveform 136.

However, in accordance with a preferred embodiment, the defibrillator 100 employs a dual capacitor circuit 142 comprising a pair of capacitors 103 comprising a first capacitor 103A and a second capacitor 103B or first and second banks of capacitors.

The charging circuit 102 may charge both capacitors 103A and 103B in series with the polarity as shown. A first electrode pad 106A may be connected between the capacitors 103.

During delivery of the biphasic waveform 136, the discharge circuit 105 may be configured to close the positive waveform switch 143 such that the positive exponential decay current 137 is applied between the second electrode pad 106B and the first electrode pad 106A.

In embodiments, the first capacitor 103A may be approximately 60 µF and therefore the discharge circuit 105 may be configured for closing the positive waveform switch 143 for approximately 7.7 ms as is substantially shown in FIG. 9 until such time that the positive exponential decay current phase 137 approaches 0 V.

At or around that time, the discharge circuit 105 may be further configured for closing a negative waveform switch 144 to apply the negative exponential decay waveform phase 138 from the second electrode pad 106B to the first electrode pad 106A. The discharge circuit 105 may open the positive waveform switch 143 when closing the negative waveform switch 144.

In embodiments, the second capacitor 103B may have less capacitance than that of the first capacitor 103A such as from approximately 20-60 µF. The second capacitor 103 may, for example, comprise 30, 40 or 50 µF such that the duration of the negative exponential decay waveform phase 138 is approximately 3.8, 5 and 6.2 ms respectively.

Figure 10:
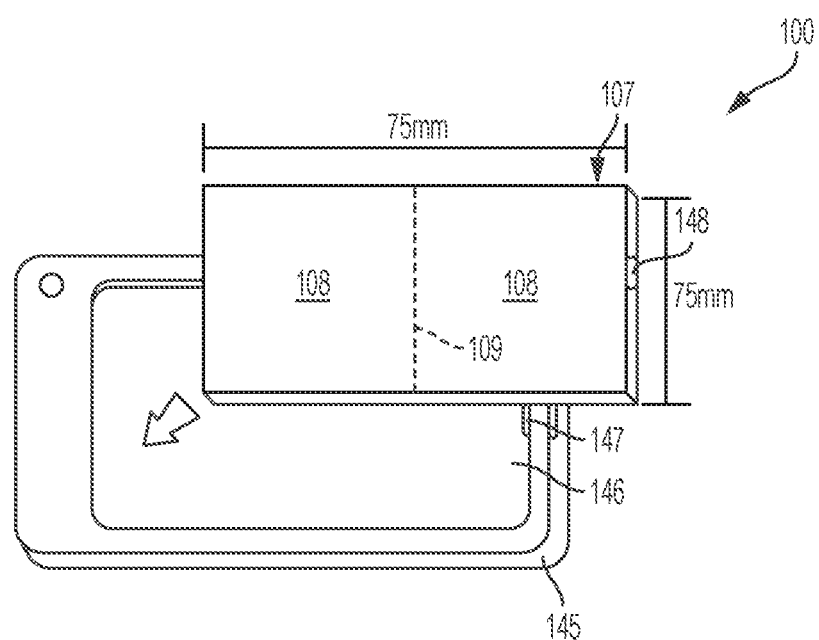
FIG. 10 illustrates a further single use defibrillator packaging in accordance with an embodiment.

FIG. 10 illustrates an embodiment wherein the defibrillator 100 comprises the bifurcated board 107 and wherein the bifurcated board 107 is configured for interfacing with a mobile phone case 145. In accordance with this embodiment, the mobile phone case 145 comprises a rear accommodation 146 within which the bifurcated board 107 is accommodated. In embodiments, the board 107 may comprise dimensions of approximately 70 mm in length, 60 mm in width and 2.5 mm in thickness. The rear accommodation 146 may have an inward projecting electrical and/or data connection 147 which may interface with a corresponding electrical and/or data interface port 148 of the board 107.

When required for use, the board 107 may be removed from the case 145, such as by bending the end of the case, sliding the board 107 therefrom and the like. As alluded to above, when removed from the case 145, the defibrillator 100 may interface via the wireless interface 116 with the mobile device 113 within the case 145 to control various operational aspects thereof.

Figure 11:
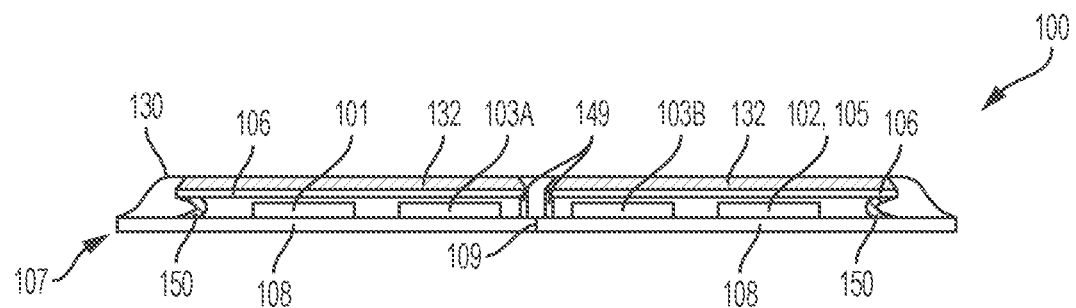
FIGS. 11-14 illustrate side elevation views illustrating the deployment of the defibrillator of the embodiment of FIG. 10.

FIG. 11 illustrates a cross-sectional elevation view of the defibrillator 100 in accordance with the embodiment of FIG. 10. There is shown the bifurcated board 107 comprising the two portions 108 and the bisection 109 therebetween. The bisection 109 may comprise a line of weakness within the board 107 such that when bent, the board 107 snaps into the two constituent portions 108.

The defibrillator 100 may further comprise the first capacitor 103 and the second capacitor 103B.

The defibrillator 100 may further comprise the controller 101 and the charge circuit 102 and the discharge circuit 105.

The electrode pads 106 may lie atop the portions 108 and, in embodiments, the various componentry shown. Electrical connections stubs 149 may electrically connect proximal edges of the electrode pads 106.

The electrode pads 106 may be flexible foil pads able to bend in the manner described hereunder. In this regard, the distal edges thereof may comprise flexible retainers 150 shown retracted in FIG. 11. The defibrillator 100 may further comprise the peel-off layer 130 covering the electrodes 106. As alluded to above, a conductive gel layer 132 may cover the electrodes 106.

Figure 12:
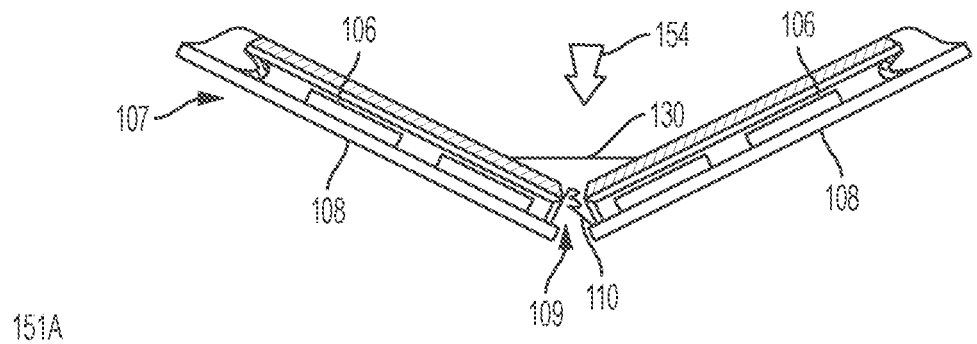

FIG. 12 illustrates pressure 151 applied to the bisection 109 causing the board 107 to snap into the two portions 108 at the boundary 109. The circuit completion wire 110 may maintain electrical connections between the portions 108 when broken apart in this manner.

Figure 13:
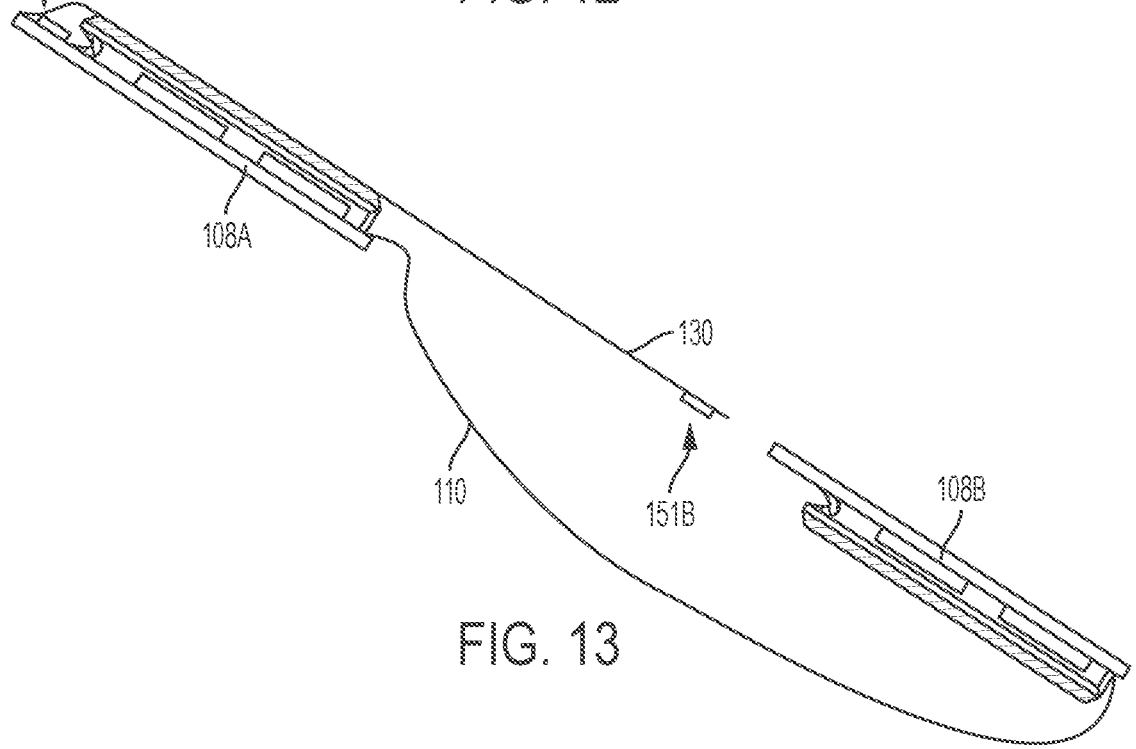

As can be seen from FIG. 12, the breaking apart of the portions 108 naturally peels the peel-off layer 130 from the electrodes 106. Specifically, FIG. 13 illustrates the 180° rotation of the second portion 108B from the first portion 108A so as to allow the peel-off layer 130 to be entirely and easily pulled from the second portion 108B from the adhesive edge 151 thereof. The first portion 108A may be similarly orientated to entirely remove the peel off layer 130 from the other sticky edge 151A. As can be seen, the circuit completion wire 110 has sufficient length for this manouver. In embodiments, the circuit completion wire 110 may comprise a length of approximately 20 cm or more.

Figure 14:
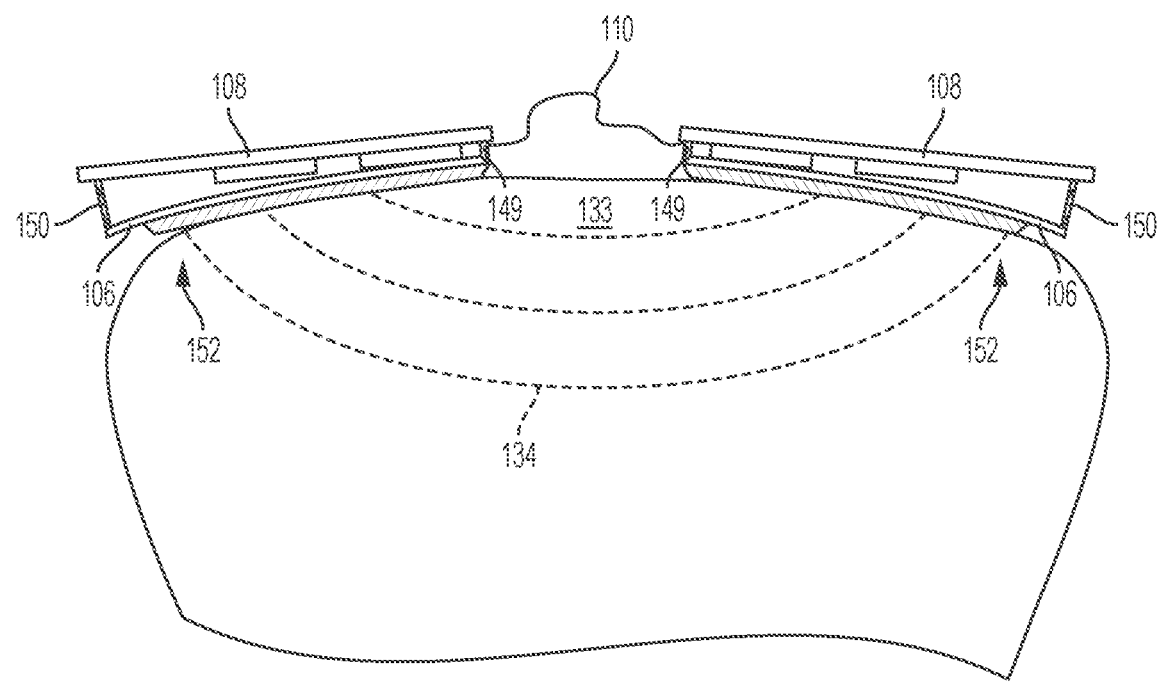

FIG. 14 illustrates the inversion of the portions 108 and the spacing apart placement thereof atop the chest 133. As can be seen, the circuit completion wire 110 completes the electric circuit for the biphasic waveform current 136 through the heart muscle 135.

As can be further seen from FIG. 14, the flexible electrode pads 106 are flexible so as to align with the curvature of the chest 133 despite the planar nature of the backing portions 108. Specifically, the flexible electrode pads 106 are electrically connected to the backing portions 108 by the electrical connections stubs 149 at the proximal ends thereof, allowing chest contour following movement tolerance to the distal edges 152 thereof.

As can be appreciated from FIG. 14, the flexible retainers 150 are taut so as to retain the distal edges of the flexible electrode pads 106.

Figure 15:
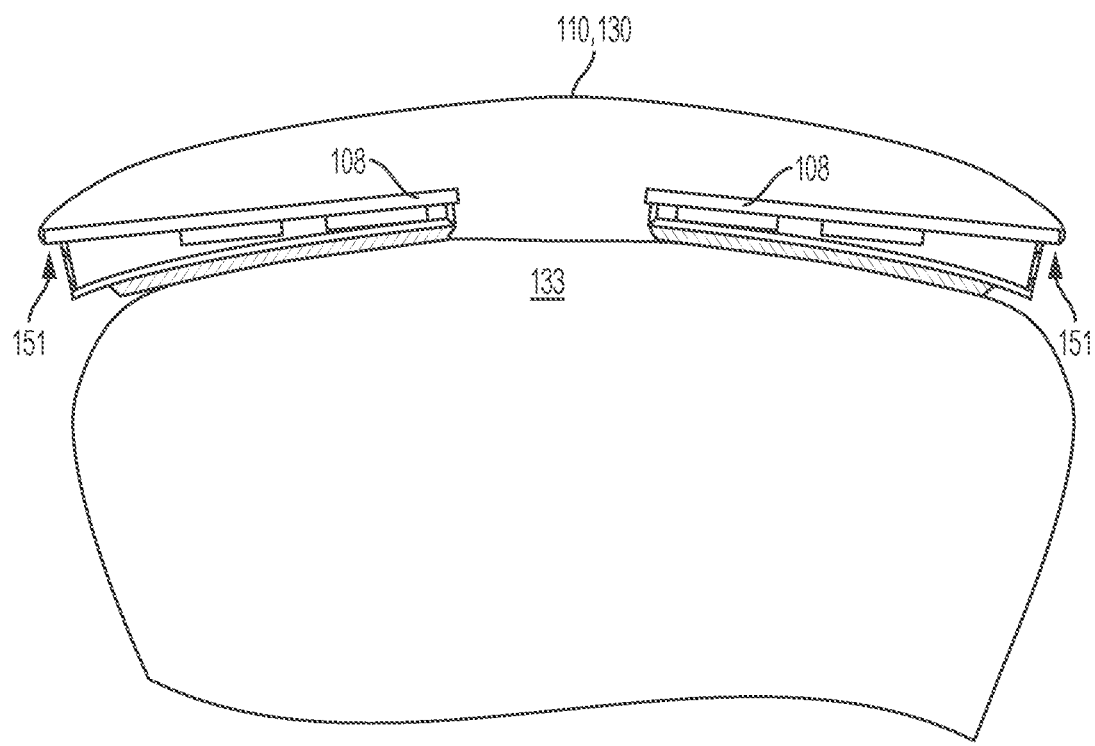
FIG. 15 illustrates a variation of the embodiment of FIG. 10 negating the need for a circuit completion wire.

FIG. 15 illustrates an embodiment wherein the peel-off layer 130 is itself electrically conductive or which comprises an integrally formed circuit completion wire 110. In accordance with this embodiment, the peel-off layer 130 remains adhered to the lateral adhesive edges 151 of the pin portions 108 so as to complete the electrical circuit therebetween. This configuration negates the need for a separate circuit completion wire 110 as described above.

Rapid deployment of the defibrillator 100 in a single hand motion may comprise holding rear edges of the board 107 may be held with the forefingers of both hands and using the thumbs opposingly to apply pressure to the board 107 at the bisection 109 so as to break the board 107 into the two portions. The motion may continue through to rotate each portion 108 through about 180° to peel off the peel-off layer 130 so as to expose the electrode pads 106 to the chest 133. For the embodiment of FIG. 15, the electrically conductive peel-off layer 130 remains electrically connected at the edges 151 thereof to complete the circuit.

As such, this quick deployment action allows the defibrillator 100 to be applied quickly to perhaps even be applied by a heart attack victim prior loss of consciousness.

In a further embodiment, the defibrillator may be provided within a rectangular housing comprising two PCB board sections located either side of the bisection 109. Substantially square tin-based electrodes 106 having an area of approximately 80 mm×164 mm may locate thereatop and may connect to electrical connections of the PCB boards by way of pinhole vias. Vertical columns may mechanically interface the PCB boards to the electrodes. A hydrogel layer may be above the electrodes 106 and the peel-off covering 130 further thereatop.

Various electronic componentry may be located underneath the PCB boards such that the opposite sides thereof may lie flush and flat against the electrodes, hydrogel layer and peel off covering 130. Furthermore, larger size components such as capacitors, batteries and the like may locate beneath the PCB boards and the rear backing of the housing, including laterally adjacent the printed circuit boards. Inner faces of the housing adjacent the bisection 109 may comprise dividing walls which may comprise apertures through which the circuit completion wire 110 is pulled. Specifically, pressure 151 applied to the housing at an upper edge thereof will cause the lower side thereof between the dividing walls to break apart and, whilst doing so, the circuit completion wire 110 will be pull therefrom.

The foregoing description, for purposes of explanation, used specific nomenclature to provide a thorough understanding of the invention. However, it will be apparent to one skilled in the art that specific details are not required in order to practice the invention. Thus, the foregoing descriptions of specific embodiments of the invention are presented for purposes of illustration and description. They are not intended to be exhaustive or to limit the invention to the precise forms disclosed; obviously, many modifications and variations are possible in view of the above teachings. The embodiments were chosen and described in order to best explain the principles of the invention and its practical applications, they thereby enable others skilled in the art to best utilize the invention and various embodiments with various modifications as are suited to the particular use contemplated. It is intended that the following claims and their equivalents define the scope of the invention.

The invention claimed is:

1. A portable automatic external defibrillator comprising: a controller;
a charging circuit controlled by the controller to charge at least one capacitor using a battery;
a discharge circuit controlled by the controller to discharge the at least one capacitor using a pair of electrode pads; and
a board separable into two portions at a line of bisection, each portion having a respective electrode pad on an upper surface thereof,
wherein each of the controller, the charging circuit, the discharging circuit, and the battery is part of or mounted to the board.

2. The defibrillator as claimed in claim 1, wherein the electrode pads are flexible and wherein the two portions are substantially rigid and wherein the electrode pads are electrically connected to respective portions at proximal edges thereof adjacent the line of bisection such that the respective opposite lateral edges thereof are free to follow chest contours.

3. The defibrillator as claimed in claim 2, further comprising flexible retainers retaining the lateral edges to respective portions.

4. The defibrillator as claimed in claim 1, wherein the controller and charging and discharging circuits are located between respective electrode pads and portions.

5. The defibrillator as claimed in claim 1, wherein the electrodes comprise electrically conductive gel layers.

6. The defibrillator as claimed in claim 1, wherein the charging circuit comprises a first capacitor and a second capacitor and wherein the controller is configured for controlling the discharge circuit to deliver a positive step change exponential decay current phase using the first capacitor and a subsequent negative step change exponential decay current phase using the second capacitor.

7. The defibrillator as claimed in claim 6, wherein the discharge circuit comprises a first switch operably coupled to the first capacitor and a second switch operably coupled to the second capacitor and wherein the discharge circuit operates the switches in turn.

8. The defibrillator as claimed in claim 6, wherein the phases each have a peak voltage amplitude of approximately 1 kV.

9. The defibrillator as claimed in claim 6, wherein the first capacitor has a greater capacitance than that of the second capacitor and wherein the positive step change exponential decay current phase has a duration greater than that of the negative step change exponential decay current phase.

10. The defibrillator as claimed in claim 6, wherein the first capacitor is 60 µF and wherein the second capacitor is between 20 and 60 µF.

11. The defibrillator as claimed in claim 6, wherein the positive exponential decay current waveform has a duration of between 6 and 9 ms.

12. The defibrillator as claimed in claim 1, wherein the pair of electrode pads comprises adjacent electrode pads, and the defibrillator further comprising a peel-off layer covering the adjacent electrode pads.

13. The defibrillator as claimed in claim 12, wherein the peel-off layer is electrically conductive and wherein the peel-off layer remains connected to lateral edges of the portions such that when the portions are broken apart and inverted to contact the chest, the peel-off layer electrically connects the portions.

14. The defibrillator as claimed in claim 1, wherein the two portions are substantially the same size.

15. A method using a portable automatic external defibrillator comprising: a controller; a charging circuit controlled by the controller to charge at least one capacitor using a battery; a discharge circuit controlled by the controller to discharge the at least one capacitor using a pair of electrode pads; a board separable into two portions at a line of bisection, each portion having a respective electrode pad on an upper surface thereof; a peel-off layer covering both electrodes, wherein each of the controller, the charging circuit, the discharging circuit, and the battery is part of or mounted to the board, the method comprising:
separating the two portions of the board at the line of bisection and rotating each portion to peel the peel-off layer from the two portions and to expose the electrode pads to place the portable automatic external defibrillator in a condition ready for use.

16. The method as claimed in claim 15, wherein the method further comprises moving the portions apart to detach the peel-off layer from both portions.

17. The method as claimed in claim 16, wherein the peel-off layer is electrically conductive and wherein the method further comprises leaving the peel-off layer electrically connected between edges of the portions.

\* \* \* \* \*